United States Patent [19]
Ghio et al.

[11] Patent Number: 5,830,436
[45] Date of Patent: *Nov. 3, 1998

[54] METHOD OF MUCOCILIARY CLEARANCE IN CYSTIC FIBROSIS PATIENTS USING ALKYLARYL POLYETHER ALCOHOL POLYMERS

[75] Inventors: Andrew J. Ghio; Claude A. Piantadcsi, both of Durham, N.C.; Thomas P. Kennedy, Richmond, Va.

[73] Assignee: Duke University, Durham, N.C.

[ * ] Notice: The term of this patent shall not extend beyond the expiration date of Pat. No. 5,474,760.

[21] Appl. No.: 413,699

[22] Filed: Mar. 30, 1995

Related U.S. Application Data

[63] Continuation-in-part of Ser. No. 219,770, Mar. 29, 1994, Pat. No. 5,474,760, which is a continuation-in-part of Ser. No. 39,732, Mar. 30, 1993, abandoned.

[51] Int. Cl.$^6$ ..................................... A61K 9/12
[52] U.S. Cl. ......................... 424/45; 424/78.37; 514/851
[58] Field of Search ................ 424/45, 78.37; 514/828, 851

[56] References Cited

U.S. PATENT DOCUMENTS

| | | | |
|---|---|---|---|
| 2,454,541 | 11/1948 | Bock et al. | 525/507 |
| 4,039,669 | 8/1977 | Beyler et al. | 514/178 |
| 4,826,821 | 5/1989 | Clements | 514/78 |
| 4,944,941 | 7/1990 | Ammann | 514/78 |
| 5,110,806 | 5/1992 | Clements | 424/855 |
| 5,134,129 | 7/1992 | Lichtenberger | 514/78 |
| 5,145,684 | 9/1992 | Liversidge, et al. | 424/489 |
| 5,259,963 | 11/1993 | Wiedemann | 252/86 |
| 5,399,363 | 3/1995 | Liversidge, et al. | 424/490 |
| 5,474,760 | 12/1995 | Ghio et al. | 424/45 |

OTHER PUBLICATIONS

Lethem et al., "The Role of Mucous Glycoproteins in the Rheologic Properties of Cystic Fibrosis Sputum," *Am. Rev. Respir. Dis.*, vol. 142, pp. 1053–1058 (1990).

Fuchs et al., "Effect of Aerosolized Recombinant Human DNase on Exacerbations of Respiratory Symptoms and on Pulmonary Function in Patients with Cystic Fibrosis," *The New England Journal of Medicine*, vol. 331, pp. 637–642 (Sep., 1994).

Correspondence from Carolann W. Hooton, Chief, Freedom of Information Office, Food and Drug Administration, dated May 27, 1994.

Information brochure from Breon Laboratories on ALEVAIRE® describing the content and indicated use of this drug, dated Nov., 1965.

Aruoma, Deoxyribose Assay For Detecting Hydroxyl Radicals, *Methods In Enzymology*, vol. 233, pp. 57–82, (1994).

Baker et al., Development Of O2 Tolerance In Rabbits With No Increase In Antioxidant Enzymes, *Journal of Applied Physiology*, vol. 66, No. 4, pp. 1679–1684, (1989).

Cantin et al., Protection By Antibiotics Against Myeloperoxidase–Dependent Cytotoxicity To Lung Epithelial Cells In Vitro, *The Journal of Clinical Investigation, Inc.*, vol. 91, pp. 38–45, (Jan. 1993).

(List continued on next page.)

*Primary Examiner*—Jyothsna Venkat
*Attorney, Agent, or Firm*—Bell Seltzer Intellectual Property Group of Alston & Bird, LLP

[57] ABSTRACT

A method and medicament for the inhibition of oxidants comprising administering a treatment effective amount of alkylaryl polyether alcohol polymers to a chemical or biologic system in need thereof. Also, a method and medicament for mucociliary clearance, inhibition of cytokine production, and inhibition of interleukin-8 production in cystic fibrosis patients. The method involves administering a treatment effective amount of alkylaryl polyether alcohol polymers to a chemical or biologic system in need thereof. The medicament is preferably administered by aerosolization into the mammalian respiratory system. The medicament may also be applied to the mammalian skin. Preferably, the medicament includes a physiologically acceptable carrier which may be selected from the group consisting of physiologically buffered saline, isotonic saline, normal saline, petrolatum based ointments and U.S.P. cold cream.

5 Claims, 3 Drawing Sheets

OTHER PUBLICATIONS

Cornforth et al., Antituberculous Effect of Certain Surface–Active Polyoxyethyleen Ethers in Mice, *Nature*, vol. 168, pp. 150–153, (1951).

Floyd et al., Sensitive Assay of Hydroxyl Free Radical Formation . . . , *Journal of Biochemical and Biophysical Methods*, vol. 10, pp. 221–235, (1984).

Floyd et al., Use of Salicylate With High Pressure Liquid Chromatography . . . , *Journal of Free Radicals in Biology & Medicine*, vol. 2, pp. 12–18, (1986).

Fuchs et al., Effect Of Aerosolized Recombinant Human DNase On Exacerbations Of Respiratory Symptoms And On Pulmonary Function In Patients With Cystric Fibrosis, *The New England Journal of Medicine*, vol. 331, No. 10, pp. 637–642, (1994).

Ghio et al., Role Of Surface Complexed Iron In Oxidant Generation . . . , *American Journal Of Physiology, Lung Cellular and Molecular Physiology 7*, vol. 263, pp. L511–L518, (Jun. 29, 1992).

Ghio, Synthetic Surfactant Scavenges Oxidants And Protects Against Hyperoxic Lung Injury, *Journal Of Applied Physiology*, vol. 77, No. 3, pp. 1217–1223, (1994).

Glassman, Hemolytic Activity of Some Nonionic Surface–Active Agents, *Science*, vol. 111, pp. 688–689, (Jun. 23, 1950).

Robert A. Greenwald, Determination of HOCl Production by Micloperoxidase, *CRC Handbook of Methods for Oxygen Radical Research*, p. 300, (1987).

Halliwell et al., Role of Free Radicals . . . , *Methods in Enzymology*, vol. 186, pp. 1–83, (1990).

Hashimoto et al., Antimetastatic Effect Of Triton WR 1339, a Nonionic Detergent, On Rat Ascites Tumors, *The Tohoku Journal Of Experimental Medicine*, vol. 128, No. 3 pp. 259–265, (Jul. 1979).

Kim et al., Reevaluation Of The Effect Of Triton X–100 On The Assay Of Superoxide Radical By The Nitrobluetetrazolium Reduction Method, *Hanguk Nonghwahak Hoechi (J. Korean Agric. Chem. Soc.)*, pp. 364–369, (1993).

Kondo et al., Triton WR–1339 As A Biological–Response Modifier In Mycobacterial Infection, *Japan Journal Medical Science Biology*, vol. 39, pp. 35–47, (1986).

Lethem, et al., The Role Of Mucous Glycoproteins In The Rheologic Properties Of Cystic Fibrosis Sputum, *AAI Respiratory Disease*, pp. 1063–1068, (1990).

Lowry et al., Protein Measurement With The Folin Phenol Reagent, *Journal Of Biological Chemistry*, vol. 193, pp. 265–275, (1951).

McCarty, An Antithrombotic Role For Nutritional Antioxidants: Implications For Tumor Metastasis And Other Pathologies, *Med–Hypotheses*, pp. 345–357, (Apr. 1986).

Matalon et al., Mitigation Of Pulmonary . . . Surfactant, *Journal Of Applied Physiology*, vol. 62, No. 2 . pp. 756–761, (Feb. 1987).

Palmer et al., The Effect Of An Aerosol Detergent In Chronic Bronchitis, *The Lancet*, pp. 611–613, (Mar. 23, 1957).

Pimm et al., Influence Of ICRF 159 and Triton WR 1339 On Metastases Of A Rat Epithelioma, *The British Journal Of Cancer*, vol. 31, No. 1, pp. 62–67, (Jan. 1975).

Polk et al., A Comparative Study Of Alevaire And A New Mucolytic Agent, Acumist In Postoperative Patients, *The Eye, Ear, Nose and Throat Monthly*, vol. 49, pp. 321–324, (Jul. 1970).

Notter, Biophysical Behavior . . . Pathophysiology, *Seminars in Perinatology*, vol. 12, No. 3, pp. 180–212, (Jul. 1988).

Ramsey et al., Efficacy Of Aerosolized Tobramycin In Patients With Cystic Fibrosis, *The New England Journal Of Medicine*, vol. 328, No. 24, pp. 1740–1746, (Jun. 17, 1993).

Tainter et al., Alevaire As A Mucolytic Agent, *The New England Journal Of Medicine*, vol. 253, pp. 764–767, (1955).

Thomassen, Regulation Of Human Alveolar Macrophage Inflammatory Cytokines By Tyloxapol: A Component Of The Synthetic Surfactant Exosurf, *Clin. Immonol. Immunopathol.*, vol. 77, No. 2, pp. 201–205, (Nov. 1995).

Tooley et al., Lung Function . . . Surfactant, *Am. Rev. Respir.–Dis.*, vol. 136, No. 3, pp. 651–656, (Sep. 1987).

Turrens et al., Protection Against Oxygen Toxicity, *Journal of Clinical Investigation*, vol. 73, pp. 87–95, (Jan. 1984).

Vasconcellos et al., Reduction In Viscosity Of Cystic Fibrosis Sputum In Vitro By Gelsolin, *Science*, vol. 263, pp. 969–971, (Feb. 18, 1994).

Wiseman et al., The Structural Mimicry Of Membrane Sterols By Tamoxifen: Evidence From Cholesterol Coefficients And Molecular–Modelling For Its Action As A Membrane Anti–Oxidant And An Anti–Cancer Agent, *Biochim–Biophys–Acta.*, pp. 197–202, (Mar. 20, 1992).

Wiseman et al., Droloxifene (3–Hydroxytamoxifen) Has Membrane Antioxidant Ability: Potential Relevance To Its Mechanism Of Therapeutic Action In Breast Cancer, *Cancer–Lett.*, pp. 61–68, (Sep. 14, 1992).

Correspondence from Carolann W. Hootan, Department Of Health & Human Services, regarding Alevaire, dated May 27, 1994, including brochure of Alevaire® dated Nov. 1965.

METHOD OF MUCOCILIARY CLEARANCE IN CYSTIC FIBROSIS PATIENTS USING ALKYLARYL POLYETHER ALCOHOL POLYMERS

RELATED APPLICATION(S)

This application is a Continuation-in-Part of applicants' application U.S. Ser. No. 08/219,770, filed Mar. 29, 1994, now issued as U.S. Pat. No. 5,474,760 on Dec. 12, 1995, which is a Continuation-in-Part of applicants' application U.S. Ser. No. 08/039,732, filed Mar. 30, 1993, now abandoned.

FIELD OF THE INVENTION

The invention in the present Continuation-in-Part relates, in general, to cystic fibrosis, the most common lethal recessive genetic disease in the United States. Cystic fibrosis is characterized by abundant production in a cystic fibrosis patient of thick, tenacious, purulent airway secretions. These secretions are difficult to clear, even with physiotherapy, and hence, obstruct airways and contribute greatly to the progression of obstructive lung disease by stagnating the inflammatory process within airways.

More particularly, the invention in the present Continuation-in-Part relates to use of alkylaryl polyether alcohol polymers, particularly tyloxapol, as mucolytic agents for breaking up cystic fibrosis sputum or mucous in patients with cystic fibrosis, as inhibitors of monocyte tumor necrosis factor secretion in patients with cystic fibrosis, and as inhibitors of production of interleukin-8 by patients with cystic fibrosis.

The parent applications of the present Continuation-in-Part, namely, U.S. Ser. No. 08/219,770 now U.S. Pat. No. 5,474,760 issued Dec. 12, 1995 and U.S. Ser. No. 08/039,732, now abandoned relate to use of alkylaryl polyether alcohol polymers as antioxidants to suppress certain oxidant chemical reactions that cause tissue injury and disease in mammals and plants.

BACKGROUND OF THE INVENTION
Discussion of Oxidant-Mediated Injury

Oxygen is life-giving to aerobic plants and animals who depend on it for energy metabolism. It can also be lethal to those same organisms when it is altered from its stable dioxygen ($O_2$) state to any one of three partially reduced species: a) the one electron reduced form superoxide anion ($O_2^-$); b) the two electron reduced form hydrogen peroxide ($H_2O_2$); or the deadly three electron reduced form hydroxyl radical (.OH). In biologic systems $O_2^-$ and $H_2O_2$ are metabolic byproducts of a host of enzymes (oxygenases) that use oxygen as a cofactor. $H_2O_2$ is also produced from $O_2^-$ by the enzymatic action of superoxide dismutases. However, .OH is generally produced only when $O_2^-$ and $H_2O_2$ interact with transitional ions of metals such as iron and copper in dangerous cyclical redox reactions:

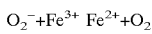

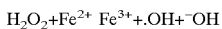

The above reaction is termed the superoxide driven Fenton reaction. The Fenton reaction can also be initiated by other reducing substances such as ascorbate in the presence of ferric iron and $H_2O_2$.

While $O_2^-$ and $H_2O_2$ are each toxic for biological systems, .OH (and its alternate hypothesized form the ferryl intermediate $FeO^{2+}$) is a highly reactive species that can oxidize unsaturated membrane lipids, damage cellular proteins and cause mutagenic strand breaks in DNA. To prevent injury from partially reduced $O_2$ species under normal conditions, cells have evolved an elaborate system of antioxidant enzymes (superoxide dismutase, catalase, glutathione peroxidase) and antioxidant molecules (glutathione, alpha-tocopherol, beta carotene). However, when production of partially reduced $O_2$ species exceeds the capacity of cellular antioxidant defenses to contain them, oxidant injury occurs.

A growing number of mammalian disease entities are now thought to be related to overproduction of partially reduced $O_2$ species, including the reperfusion injury syndromes myocardial infarction and stroke, adult respiratory distress syndrome, oxygen toxicity of the lung, lung injury from asbestos, Parkinson's disease, thermal and solar burns of the skin, and injury to the gastrointestinal tract from nonsteroidal anti-inflammatory agents (see Table IV, page 60, Halliwell B and Gutteridge JMC. *Methods in Enzymology* (1990) 186:1–85). Treatment of these conditions is increasingly directed either toward strategies that prevent enzymatic production of partially reduced $O_2$ species and to the introduction of exogenous antioxidant compounds that restore oxidant-antioxidant balance in biologic and chemical systems.

Also, studies by the present inventors, as described in more detail below, suggest that airway cells in cystic fibrosis patients are at risk of oxidant-mediated injury. The reason is that the leukocyte-derived enzyme, myeloperoxidase, present in large amounts in the bronchial secretions of cystic fibrosis patients, converts with $H_2O_2$ produced by polymorphonuclear leukocytes to HOCl/OCl, the major leukocyte-derived oxidant.

Discussion of Cystic Fibrosis

The hallmark of cystic fibrosis is abundant production in a cystic fibrosis patient of thick, tenacious, purulent airway secretions that are difficult to clear, even with physiotherapy. These secretions obstruct airways and contribute greatly to the progression of obstructive lung disease by stagnating the inflammatory process within airways.

Surprisingly, the present inventors have found that a mucolytic agent, namely tyloxapol, used years ago in treatment of adult chronic bronchitis (see, discussion below vis-a-vis withdrawal of ALEVAIRE® from the market place by the Food and Drug Administration) dramatically reduces the viscoelastic properties of cystic fibrosis sputum (see, Example IV below).

Cystic fibrosis is the most common lethal recessive genetic disease in the United States. (See, Di Sant' Agrese and Davis, "Cystic Fibrosis in Adults: 75 Cases and a Review of 232 Cases in the Literature," *Am J. Med.* (1979) 66:121–132.) It is a disease primarily affecting those of northern European ancestry, and occurs once in every 1500 to 2000 Caucasian live births and once in every 17,000 Afro-American live births in the United States. (See, Steinbert and Brown, "On the Incidence of Cystic Fibrosis on the Pancreas," *Am. J. Human Genet.* (1969) 12:416–424; Kramm, Crane, Sinkin, and Brown, "A Cystic Fibrosis Pilot Survey in Three New England States," *Am. J. Public Health* (1962) 52:2041–2051; Merritt, Hanna, Todd, and Myers, "The Incidence and Mode of Inheritance of Cystic Fibrosis," *J. Lab. Clin. Med.* (1962) 60:990–999; and Shultz, Schlisinger, and Moser, "The Erie County Survey of Long Term Childhood Disease," *Am. J. Public Health* (1966) 56:1461–1469.) About 5% of the population of the United States are carriers for the cystic fibrosis recessive gene. (See, Kramm et al., supra.) Of patients with cystic fibrosis, about 50% die before reaching the age of 21 years. (See, Di Sant' Agrese and Davis, "Research in cystic Fibrosis," *New England J. Med.* (1976) 295:481–488.) Accordingly, any intervention that improves the prognosis in this disease would have a major impact on childhood and adolescent mortality and morbidity from cystic fibrosis in the United States.

The major cause of mortality and morbidity in patients with cystic fibrosis is progressive pulmonary disease. (See, Stern, Boat, Doershuk, Tucker, Psimiano, and Matthews, "Course of Cystic Fibrosis in 95 Patients," *J. Pediatrics* (1976) 89:406–411.) Lung disease is not present at birth, but develops later, during childhood or adolescence. (See, Sturgess and Imrie, "Quantitative Evaluation of the Development of Tracheal Submucosal Glands in Infants with Cystic Fibrosis and Control Infants," *Am. J. Pathol.* (1992); 106:303–311; Davis, "Pathophysiology of Pulmonary Disease in Cystic Fibrosis," *Seminars Respir. Med.* (1985) 6:261–270; and Wood, Boat, and Doershuk, "Cystic Fibrosis," *Am. Rev. Respir. Dis.* (1969) 113:833–878.)

While the earliest events in the pathogenesis of cystic fibrosis lung disease are uncertain, inflammation of small airways is an early lesion. (See, Davis, supra.) The inflammation may be caused by early infection since patients with cystic fibrosis have distinctive respiratory flora. (See, Mearns, Hunt, Rushworth, "Bacterial Flora of the Respiratory Tract in Patients with Cystic Fibrosis, 1950–1971," *Arch. Dis. Child* (1972) 47:902–907; and May, Herrick, and Thompson, "Bacterial Infections in Cystic Fibrosis," *Arch. Dis. Child* (1972) 47:908–913.)

*Staphylococcus aureus* is generally the dominant organism early in the course of cystic fibrosis disease, and is supplanted later by *Pseudomonas aeruginosa*, especially mucoid strains. (See, Tococca, Sibringo, and Barbeso, "Respiratory Tract Bacteriology in Cystic Fibrosis," *Am. J. Dis. Child* (1963) 106:315–325; and Doggett, Harrison, Stillwell, and Wallis, "An Atypical *Pseudomonas aeruainose* Associated with Cystic Fibrosis of the Pancreas," *J. Pediat.* (1966) 68:215–221.)

As infections and inflammation become established in airways of the cystic fibrosis patient, hypertrophy and hyperplasia of the mucous-secreting apparatus develops, ciliated cells are replaced by goblet cells, and squamous metaplasia becomes pronounced. Beneath impacted mucous, denudation and ulceration of the mucosa may occur. Gradually, this destruction progresses up the respiratory tree to involve the larger airways. Structural damage to the bronchial wall occurs, and bronchiectasis develops. Bronchiectasis and mucopurulent plugging are present in most cystic fibrosis patients who come to necropsy after the age of 2 years. (See, Bedrossian, Greenberg, and Gisner, "The Lung in cystic Fibrosis," *Human Pathol.* (1976) 7:195–204.)

Several factors contribute to the progression of lung disease in cystic fibrosis patients, but important among them is the thick, viscous nature of airway mucous. Not only do thick secretions obstruct airways and contribute to reduced lung volumes and expiratory flows, but they also cause the inflammatory process to stand within the airways, thereby exposing the airway mucosa to a more abundant protease and oxidant rich environment than if the purulent respiratory secretions were easily expectorated. The enhanced viscoelastic properties of purulent secretions is due in part to the presence of highly polymerized, polyanionic deoxyribonucleic acid (DNA) from the nuclei of degenerating polymorphonuclear neutrophils (PMNs). (For a discussion of the characteristics of the mucous or sputum from cystic fibrosis patients, see, for instance, Lethem et al. "The Role of Mucous Glycoproteins in the Rheologic Properties of Cystic Fibrosis Sputum," *Am. Rev. Respir. Dis.* (1990) 142:1053–1058.)

Also, contributing to sputum tenacity is the presence of abundant cross-linked actin filaments from the cytosol of PMNs. Strategies to reduce the viscoelasticity of cystic fibrosis sputum and render it more easily expectorated include aerosol administration of recombinant human DNase I (rhDNase), which is a naturally occurring extracellular enzyme, to lyse DNA, or aerosol administration of gelsolin, which is a normal intracellular severing protein, to depolymerize actin. (For a discussion of treatment of cystic fibrosis, see, for instance, Cantin et al. "Protection by Antibiotics Against Myeloperoxidase-Dependent Cytotoxicity to Lung Epithelial Cells in Vitro," *Journal of Clinical Investigation* (January, 1993) 91:38–45; Ramsey et al., "Efficacy of Aerosolized Tobramycin in Patients with Cystic Fibrosis," *The New England Journal of Medicine* (June, 1993) 328:1740–1746; Vasconcellos et al., "Reduction in Viscosity of Cystic Fibrosis Sputum in Vitro by Gelsolin," *Science* (February, 1994) 263:969–971; Hubbard, McElvaney, and Birrer, "A Preliminary Study of Aerosolized Recombinant Human Deoxyribonuclease I in the Treatment of Cystic Fibrosis," *New England J. Med.* (1992) 326:812–815; Ranasinha, Assoufi, and Shak, "Efficacy and Safety of Short-Term Administration of Aerosolized Recombinant Human DNase I in Adults with Stable Stage Cystic Fibrosis," *Lancet* (1993) 342:199–202; Ramsey, Astley, and Aitken, "Efficacy and Safety of Short-Term Administration of Aerosolized Recombinant Human Deoxyribonuclease in Patients with Cystic Fibrosis," *Am. Rev. Respir. Dis.* (1993) 148:145–151; and Fuchs et al. "Effect of Aerosolized Recombinant Human DNase on Exacerbations of Respiratory Symptoms and on Pulmonary Function in Patients with Cystic Fibrosis," *The New England Journal of Medicine* (September, 1994) 331:10:637–642.)

Although not mentioned in those of the articles cited in the above paragraph that discuss treatment of cystic fibrosis sputum with DNase, it is noted that it is well known that DNase treatment costs about $10,000 per year per patient. Discussion of Alkylaryl Polyether Alcohol Polymers, Including Tyloxadol It is additionally noted that alkylaryl polyether alcohol polymers are a known class of polymers and are used commercially as surface active detergents and wetting agents (U.S. Pat. No. 2,454,541, issued in 1948 to Bock and Rainey, assignors to Rohm & Haas). A structure representative of the class of compounds is shown in FIG. 1. The best known of this class is tyloxapol, a polymer of 4-(1,1,3,3-tetramethylbutyl)phenol with formaldehyde and oxirane.

Moreover, tyloxapol is relatively nontoxic and does not hemolyze red blood cells in a thousand times the concentrations at which other detergents are hemolytic (Glassman H N. *Science* (1950) 111:688–689). Tyloxapol has been used in human pharmacologic formulations for over 30 years (Tainter M L et al. *New England Journal of Medicine* (1955) 253:764–767).

For instance, a composition sold by Winthrop Laboratories (a division of Sterling Drug, Inc.) and by Breon Laboratories (a subsidiary of Sterling Drug, Inc.) under the trademark ALEVAIRE®, containing 0.125% SUPERINONE® (brand of tyloxapol) in combination with 2% sodium bicarbonate and 5% glycerin, had been marketed for about 30 years for treatment of mucous secretions in patients with diseases and disorders such as chronic bronchitis, croup, pertussis, and poliomyelitis. (See, for example, a product brochure entitled "ALEVAIRE® Detergent Aerosol for Inhalation" (November, 1965) distributed by Breon Laboratories.)

However, in December of 1981, ALEVAIRE® was withdrawn by the Food and Drug Administration for lack of efficacy for treatment of mucous secretions in patients with diseases and disorders such as chronic bronchitis, croup, pertussis, and poliomyelitis because it was found that there was no evidence that the tyloxapol in ALEVAIRE® had any effect on secretions in the lung from diseases such as chronic bronchitis other than that of water in thinning secretions by simple dilution, and that papers in the manufacturer's bibliography were based on clinical impression and did not reflect adequate controls. (See, letter dated May 27, 1994 to Dr. Thomas Kennedy, one of the co-inventors of the present application, from Ms. Carolann W. Hooton, Chief, Freedom of Information Office, Center for Drug Evaluation and Research, Department of Health & Human Services, Public Health Service, Food and Drug Administration, Rockville, Md.)

Synopsis of Backgroud Discussion

Antioxidants are compounds that can be easily oxidized to stable chemical forms. They can protect chemical and biologic systems by sacrificing themselves to oxidation in preference to oxidation of critically important chemical and biologic molecules. Not all oxidizable compounds can perform an antioxidant function. To successfully protect chemical and biologic systems from oxidants, the antioxidant must have a higher reactivity for the oxidant than the chemical or biologic molecule which it seeks to protect. It is theoretically possible to synthesize a multitude of compounds with antioxidant properties. However, the factor limiting use of these antioxidants as treatments in biologic systems is the inherent toxicity of the antioxidant compounds themselves.

Thus, it is a major advantage to discover that a class of commonly used and nontoxic ingredients in medicinal pharmacologic preparations are also potent antioxidants. Not only can such compounds react with partially reduced $O_2$ species, but they can be used as treatments for oxidant mediated diseases without themselves causing toxicity to biologic systems. Additionally, it is a major advantage to discover that for a patient with cystic fibrosis, they can be used as mucociliary clearance agents for cystic fibrosis sputum, as inhibitors of monocyte tumor necrosis factor secretion, and as inhibitors of production of interleukin-8.

SUMMARY OF THE INVENTION

As explained below, this invention in the present Continuation-in-Part describes how alkylaryl polyether alcohol polymers, such as tyloxapol, are useful as treatment agents for mucociliary clearance, as inhibitors of monocyte tumor necrosis factor secretion, and as inhibitors of production of interleukin-8 in cystic fibrosis patients. Administration may be the same as described in U.S. Ser. No. 08/219,779 and U.S. Ser. No. 08/039,732 (which describe how alkylaryl polyether alcohol polymers are useful as antioxidants in blocking oxidant reactions and biologic injury from partially reduced $O_2$ species) and is repeated below for clarity.

It is the object of the present invention to provide a method to inhibit oxidant chemical reactions caused by partially reduced $O_2$ species.

It is a further object of the present invention to provide a method to protect mammalian tissues against injury from partially reduced $O_2$ species.

It is a further object of the present invention to provide a method and a medicament for the treatment of cystic fibrosis in patients having the disease to protect the patients from airway injury by HOCl/OCl, which for convenience, is referred to herein also as HOCl.

It is a further object of the present invention to provide a method for inhibiting oxidant chemical reactions caused by partially reduced $O_2$ species by aerosol treatment with the therapeutic agent.

It is a further object of the present invention to provide a method for inhibiting oxidant chemical reactions caused by partially reduced $O_2$ species by topical application of the therapeutic agent to the skin.

It is a further object of the present invention to provide a method and a medicament for the mucociliary clearance of cystic fibrosis sputum in patients having cystic fibrosis to protect the patients from airway injury, for instance, by aerosol treatment with the medicament.

It is a further object of the present invention to provide a method and a medicament for the inhibition of monocyte tumor necrosis factor secretion, (thus, ameliorating the cachexia and/or anexoria suffered by patients with cystic fibrosis lung disease) and for the reduction of airway injury by inhibiting local production of the chemoattractant interleukin-8.

It is an advantage of the present invention that the therapeutic agent is produced from a toxicologically characterized class of compounds with low toxicologic potential to biologic systems.

Consideration of the specification, including the several figures and examples to follow will enable one skilled in the art to determine additional objects and advantages of the invention.

The present invention provides a medicament for the inhibition of injurious effects of partially reduced $O_2$ species in chemical and biologic systems comprising a treatment effective amount of tyloxapol and related alkylaryl polyether alcohol polymers.

Also, the present invention provides a method and medicament comprising administering to a mammal having cystic fibrosis a treatment effective amount of tyloxapol and related alkylaryl polyether alcohol polymers.

In preferred embodiments of the invention, the medicament is directly instilled into the respiratory system and administered by aerosolization. In this embodiment, the medicament preferably includes a physiologically acceptable carrier which may be selected from the group consisting of physiologically buffered saline, isotonic saline, and normal saline and an additional treatment effective amount of cetyl alcohol. The pH of the alkylaryl polyether alcohol polymer and carrier mixture is preferably greater than 6.5 but equal to or less than 7.4.

In other preferred embodiments of the invention, the medicament is applied topically to the skin. In this embodiment, the medicament preferably includes a physiologic carrier selected from a commercially available petrolatum based ointment or U.S.P. cold cream.

BRIEF DESCRIPTION OF THE DRAWINGS

Reference to the following detailed description may help to better explain the invention in conjunction with the drawings in which.

DETAILED DESCRIPTION OF THE INVENTION

Figure 1:
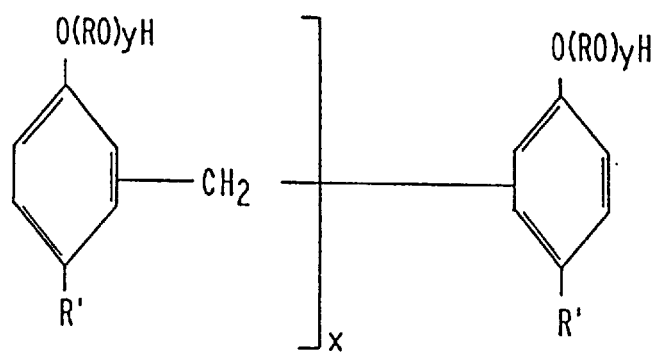
FIG. 1 shows the proposed structure of the class of compounds known as alkylaryl polyether alcohol polymers, wherein R=ethylene, R1=tertiary octyl, x is greater than 1, and y=8 to 18.

Alkylaryl polyether alcohol polymers can in general be synthesized by condensing alkylaryl alcohols with formaldehyde, as described by Bock and Rainey in U.S. Pat. No. 2,454,541 (1948, assigned to Rohm & Haas), the disclosure of which is incorporated herein by reference. All alkylaryl polyether alcohol polymers disclosed in this patent should work in the present invention. Several specific alkylaryl polyether alcohol polymers can be easily synthesized by methods previously described (J. W. Conforth et al. *Nature* (1951) 168:150–153). The structure of the alkylaryl polyether alcohol polymers used in the invention is disclosed in FIG. 1, where, R=ethylene, R'=tertiary octyl, x is greater than 1, and y=8 to 18. The prototype compound of this class, tyloxapol, can be conveniently purchased in pharmacologically acceptable purity from Rohm and Haas Co., Philadelphia, Pa.

Treatment of cystic fibrosis patients for mucociliary clearance of cystic fibrosis sputum, inhibition of monocyte tumor necrosis factor secretion, and inhibition of production of interleukin-8 with alkylaryl polyether alcohol polymers, particularly tyloxapol, is essentially the same as the administration described in U.S. Ser. No. 08/219,779 now U.S. Pat. No. 5,474,760 and U.S. Ser. No. 08/039,732 now abandoned.

More specifically, for treatment of mammalian respiratory conditions related to overproduction of partially reduced $O_2$ species, and for mucociliary clearance of cystic fibrosis sputum, inhibition of monocyte tumor necrosis factor secretion, and inhibition of production of interleukin-8, the alkylaryl polyether alcohol polymer is dissolved in sterile 0.9% NaCl for injection, and the pH is adjusted to approximately 7.0 by addition of NaOH or HCl. A nonpolymeric alkyl or aryl alcohol such as cetyl alcohol (hexadecanol) may be added equivalent to 1 to 1.5 times the weight of tyloxapol to increase the effectiveness of the mixture in protection against oxidant injury.

This mixture is then administered to the lung by direct instillation into the respiratory system. The mixture may also be administered by aerosolization using a clinically available positive pressure driven nebulizer that produces respirable particles of less than 5 microns mass median diameter.

As an example, a 0.125% solution of tyloxapol is made in sterile 0.9% NaCl and double glass distilled deionized water to make it isotonic with respect to respiratory secretions. The pH is adjusted to approximately 7.0 to prevent bronchospasm from extremes of acidity or alkalinity. This mixture is sterilized by vacuum filtration through a 0.22 micron Millipore filter and 3.3 ml each is packaged into 5 ml unit dose glass vials with rubber stoppers fastened with aluminum crimp-on "flip-tear" seals. To provide additional sterilization of product, unit dose vials are terminally autoclaved 12–14 minutes at 125 degrees Centigrade. A 5% concentration of glycerol may be optionally added to the above mixture to stabilize droplet size during aerosolization.

For administration of treatment effective doses, 3 ml of sterile tyloxapol solution is inhaled as an aerosol every 4 to 6 hours using a clinically available positive pressure driven nebulizer (Acorn or deVilbiss). Alternatively, the mixture can be nebulized into the respiratory delivery circuit of a mechanical ventilator. A beta sympathetic agonist bronchodilator (such as 1.25 to 2.5 mg of albuterol) can be mixed with the tyloxapol solution and nebulized concomitantly to prevent any transient bronchospasm that might occur from the tyloxapol solution itself.

For treatment of cutaneous oxidant-mediated disorders such as solar burn, a 0.5 to 5% mixture (w/w) is made with an alkylaryl polyether alcohol such as tyloxapol in a commercially available petrolatum based ointment such as Aquaphor (Beiersdorf, Inc., Norwalk, Conn.), white petrolatum or U.S.P. cold cream as the base vehicle. This mixture is rubbed lightly onto the affected skin area 3 to 4 times daily.

In order to facilitate a further understanding of the invention, the following examples primarily illustrate certain more specific details thereof.

Example I demonstrates the potent activity of alkylaryl polyether alcohol polymers as .OH inhibitors in chemical systems. Example II demonstrates the therapeutic benefit of using alkylaryl polyether alcohol polymers to prevent mammalian lung injury from exposure to 100% oxygen. Example III demonstrates the potent activity of alkylaryl polyether alcohol polymers as scavengers of HOCl in chemical systems. Example IV demonstrates the activity of tyloxapol as a mucolytic agent for sputum from cystic fibrosis patients. Example V demonstrates suppression of cytokine production and of interleukin-8 production.

EXAMPLE I

Inhibitions of Oxidants Generated by the Fenton Reaction

The first chemical system used to test the antioxidant activity of alkylaryl polyether alcohol polymers employed salicylate as the target molecule of oxidants. Hydroxyl radical reacts with salicylic acid (2-hydroxybenzoic acid) to produce two dihydroxybenzoic acid products, 2,3- and 2,5-dihydroxybenzoic acid. These hydroxylated products provide evidence of .OH generation (R. A. Floyd et al. *Journal of Biochemical and Biophysical Methods* (1984) 10:221–235; R. A. Floyd et al. *Journal of Free Radicals in Biology & Medicine* (1986) 2:13–18).

The detection of 2,3- and 2,5-dihydroxybenzoic acid was performed using high performance liquid chromatography with electrochemical detection. Suspensions of 10 uM $FeCl_3$, 1.0 mM $H_2O_2$, 1.0 mM ascorbate, and 10.0 uM salicylic acid were employed to generate and detect .OH. Either 0.1 ml of normal saline or tyloxapol (final concentrations of 0.0 to 10 mg/ml) were added. The reaction mixtures were incubated at 45 degrees Centigrade for 30 min and centrifuged at 1200 g for 10 min. Supernatant was centrifuged (Beckman Microfuge E) through a 0.22 uM microfuge tube filter (PGC Scientific No. 352-118) at 15,000 g.

Figure 2:
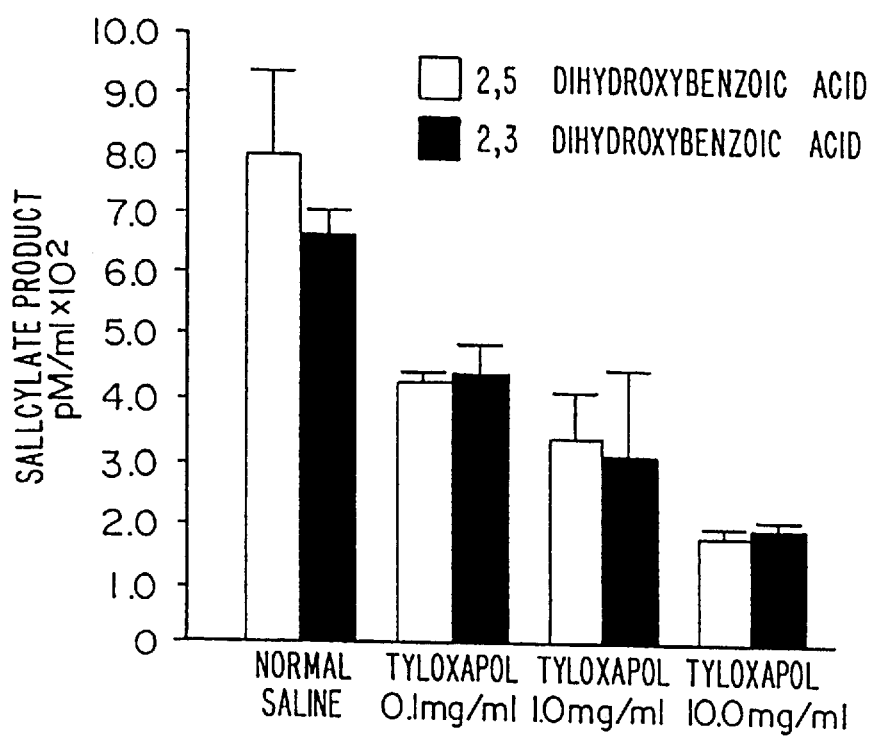
FIG. 2 shows a graph of the inhibitory effect of tyloxapol on .OH generation by the Fenton reaction, as measured by hydroxylation of salicylate.

A 100 uL sample of the eluate was injected onto a C18 RP HPLC column (250×4.7 mm, Beckman No. 235329). Hydroxylated products of salicylate were quantified with a Coulochem electrochemical detector (ESA model 5100A) with the detector set at a reducing potential of −0.40 VDC. The guard cell (used as a screen) was set at an oxidizing potential of +0.40 VDC. Measurements were done in duplicate. FIG. 2 shows that the addition of tyloxapol to the reaction mixture inhibited .OH generation in a concentration dependent manner.

The second chemical system used to test the antioxidant activity of alkylaryl polyether alcohol polymers employed 2-deoxyribose as the target molecule of oxidants. This pentose sugar reacts with oxidants to yield a mixture of products. On heating with thiobarbituric acid (TBA) at low pH, these products form a pink chromophore that can be measured by its absorbance at 532 nm (B. Halliwell and J. M. C. Gutteridge. *Methods in Enzymology* (1990) 186:1–85).

The chemical system employed to generate oxidants was a reaction mixture containing 10.0 uM $FeCl_3$, 1.0 mM ascorbate, 1.0 mM $H_2O_2$, and 1.0 mM deoxyribose in Hanks Balanced Salt Solution. This system is useful for measuring site-specific .OH generation on biologic molecules, as described by Halliwell and Gutteridge in the reference immediately above. Either 0.1 ml of normal saline or tyloxapol (final concentrations of 0.0 to 10.0 mg/ml) were added.

Figure 3:
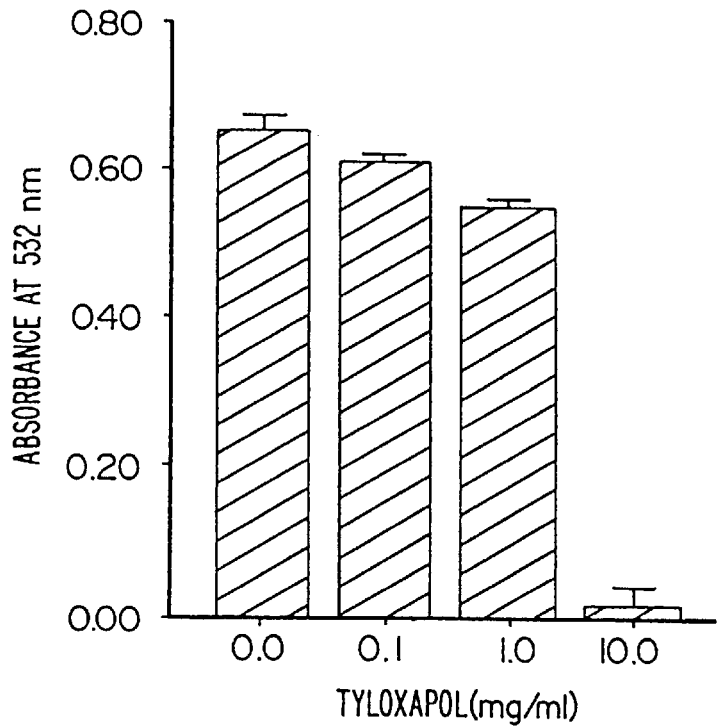
FIG. 3 shows a graph of the inhibitory effect of tyloxapol on .OH generation by the Fenton reaction, as measured by oxidation of the sugar, 2-deoxyribose.

The reaction mixtures were incubated at 45 degrees Centigrade for 30 min and centrifuged at 1200 g for 10 min. One ml of both 1.0% (w/v) TBA and 2.8% (w/v) trichloroacetic acid were added to 1.0 ml of supernatant, heated at 100 degrees Centigrade for 10 min, cooled in ice, and the chromophore determined in triplicate by its absorbance at 532 nm. FIG. 3 shows that the addition of 10 mg/ml tyloxapol to the reaction mixture causes marked inhibition of the oxidation of deoxyribose, as measured by absorbance of the oxidant reaction produced at 532 nm.

The third system used to test the antioxidant activity of alkylaryl polyether alcohol polymers employed asbestos as the source of iron for oxidant generation and 2-deoxyribose as the target molecule of oxidants. The generation of oxidants by asbestos has been described previously (A. J. Ghio et al. *American Journal of Physiology* (*Lung Cellular and Molecular Physiology* 7) (1992) 263:L511–L518). The reaction mixture, in a total volume of 2.0 ml phosphate-buffered saline (PBS), contained the following reagents: 1.0 mM deoxyribose, 1.0 mM $H_2O_2$, 1.0 mM ascorbate, and 1.0 mg/ml crocidolite asbestos. The mixture was incubated at 37 degrees Centigrade for 1 h with agitation and then centrifuged at 1,200 g for 10 min.

Oxidant generation was assessed by measuring TBA reactive products of deoxyribose as detailed in the paragraph above. Measurements were done in triplicate. TABLE I below shows that the addition of tyloxapol inhibited in a concentration dependent manner the generation of oxidants by asbestos, as measured by absorbance of the oxidant reaction product at 532.

TABLE I

Effect of Tyloxapol on Oxidant Generation by Asbestos

|  | Absorbance at 532 nm |
|---|---|
| Tyloxapol 0.0 mg/ml | 0.93 ± 0.02 |
| Tyloxapol 0.1 mg/ml | 0.89 ± 0.04 |
| Tyloxapol 1.0 mg/ml | 0.75 ± 0.01 |
| Tyloxapol 10.0 mg/ml | 0.53 ± 0.04 |

EXAMPLE II

Protection from Mammalian Lung Injury by 100% Oxygen

To determine if alkylaryl polyether alcohol polymers could protect against oxidant injury to intact biologic systems, this treatment was studied in a well established model of oxygen toxicity to the lung (J. F. Turrens et al. *Journal of Clinical Investigation* (1984) 73:87–95). Sixty-day old male Sprague-Dawley rats (Charles River, Inc., Wilmington, Mass.) were tracheally instilled with 0.5 ml of either normal saline, tyloxapol (6.0 mg) or tyloxapol (6.0 mg) and cetyl alcohol (hexadecanol, 11.0 mg). These rats (n=10 in each treatment group) were then exposed to either air or 100% oxygen in plexiglass chambers at a flow rate of 10 liters/min.

Oxygen percentage was monitored by a polarographic electrode and maintained continuously above 98%. Temperature was maintained between 20 and 22 degrees Centigrade. Survival times were determined by checking animals every 4 hours. Separate groups of rats treated similarly (n=10 in each treatment group) were exposed to 100% oxygen for 61 hours, and then were euthanized with 100 mg/kg intraperitoneal pentobarbital. Pleural fluid volume was measured by aspirating pleural fluid from the chest cavity through a small incision in the diaphragm. Lung wet/dry weight ratios were calculated from the left lung after drying the tissue for 96 hours at 60 degrees Centigrade. Survival data is shown TABLE II below.

Rats receiving intratracheal tyloxapol had markedly improved survival compared to placebo control animals instilled with saline. The protective effect of tyloxapol was further enhanced by combining it with cetyl alcohol.

TABLE II

Effect Of Tyloxapol On Oxygen Toxicity In Rats

| | Percent Survival | | |
|---|---|---|---|
| Hours | Saline | Tyloxapol | Tyloxapol/Cetyl Alcohol |
| 0 | 100 | 100 | 100 |
| 58 | 100 | 100 | 100 |
| 62 | 83 | 100 | 100 |
| 66 | 42 | 100 | 100 |
| 70 | 17 | 75 | 100 |
| 72 | 17 | 75 | 100 |
| 76 | 8 | 58 | 100 |
| 80 | 8 | 58 | 100 |
| 84 | 8 | 58 | 100 |
| 88 | 8 | 58 | 100 |
| 92 | 0 | 58 | 100 |
| 96 | 0 | 58 | 100 |

Figure 4:
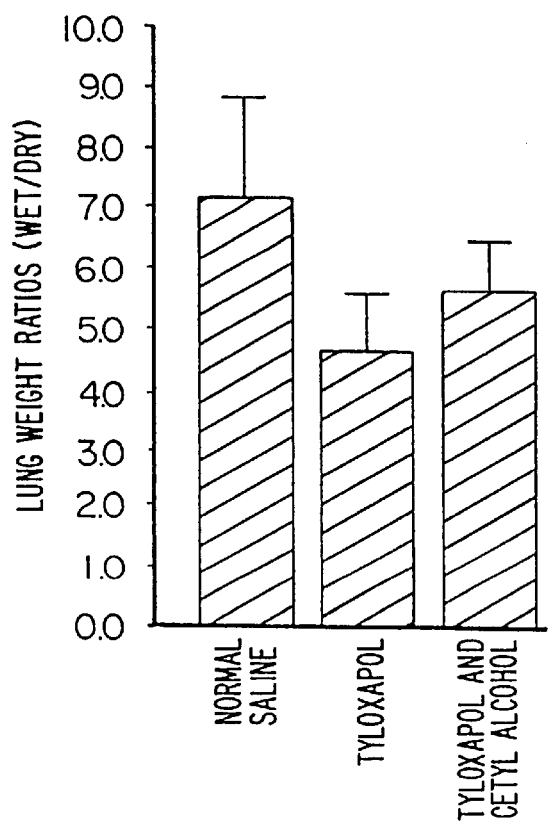
FIG. 4 shows lung wet/dry weight ratios in rats exposed to 100% oxygen and treated with normal saline, tyloxapol, and tyloxapol plus cetyl alcohol.
Figure 5:
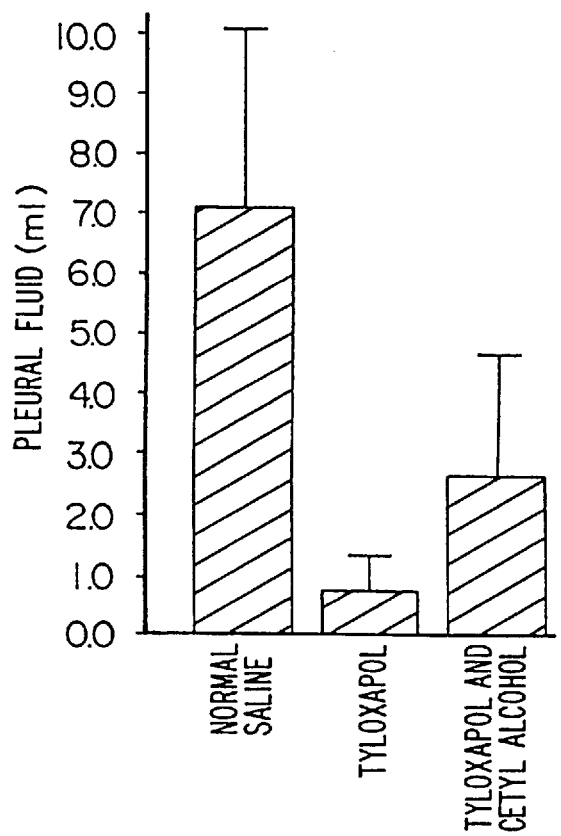
FIG. 5 shows pleural fluid accumulation in rats exposed to 100% oxygen and treated with normal saline, tyloxapol, and tyloxapol plus cetyl alcohol.

Lungs wet/dry weight ratios were substantially lower in rats treated with tyloxapol or tyloxapol and cetyl alcohol (FIG. 4), demonstrating that tyloxapol or the combination of tyloxapol and cetyl alcohol protect against edema formation from oxidant injury. Rats treated with tyloxapol or the combination of tyloxapol and cetyl alcohol also had less pleural fluid accumulation than saline treated controls (FIG. 5).

These results demonstrate the ability of alkaryl polyether alcohol polymers such as tyloxapol to protect against oxidant tissue injury. The survival studies (TABLE II) further demonstrate that the protective effect of the medicament is enhanced by combining it with alcohols such as cetyl alcohol.

EXAMPLE III

Scavenging of HOCl

The activity of tyloxapol to scavenge $OCL^{-1}$ was tested studying its ability to prevent $OCl^{-1}$-medicated oxidant conversion of diethanolamine to its corresponding chloramine ("Determination of HOCl Production by Micloperoxidase", Robert A. Greenwald, editor, *Handbook of Methods for Oxygen Radical Research*, CRC Press, Boca Raton, Fla. (1987), page 300).

The reaction mixture comprised 0.9 ml of 10.0 mM diethanolamine in 0.1M sodium acetate buffer, pH of 4.5. To this resultant was added either 100 microliters of 0.1M NaCl or tyloxapol in 0.1M NaCl, and the baseline absorbance was read at 280 nm. NaOCl was added to a final concentration of 10 mM.

The reaction mixture was incubated 15 minutes, and the absorbance was measured at 280 nm. The difference in $A_{280}$ before and after addition of NaOCl was used as a measure of concentration of the stable chloramine. Experiments were performed in triplicate. Results are summarized in Table III below.

TABLE III

| Microliters of Tyloxapol (10 mg/ml) | Absorbance (Mean ± SD) |
|---|---|
| 0 | 0.505 ± 0.002 |
| 25 | 0.468 ± 0.008 |
| 50 | 0.444 ± 0.023 |
| 75 | 0.377 ± 0.010 |
| 100 | 0.319 ± 0.025 |

Thus, tyloxapol is a potent inhibitor of the oxidant activity of HOCl, and should be useful in preventing HOCl-medicated oxidant injury of the airway in diseases such as cystic fibrosis. Administration of tyloxapol by tracheal installation to cystic fibrosis patients should inhibit HOCl produced in these patients and therefore protect them from oxidant injury. The result should be even better if some cetyl alcohol is admixed with the tyloxapol; preferably, the cetyl alcohol is added in 1 to 1.5 times the weight of the tyloxapol.

Preparation of samples for administration to the patient should be the same as described above in the "DETAILED DESCRIPTION OF THE INVENTION" section herein, most preferably inhalation of 3 ml of a 0.125% solution of tyloxapol by jet aerosol every 4 to 6 hours.

EXAMPLE IV

Treatment of Sputum from Cystic Fibrosis Patients with Tyloxapol

For testing with tyloxapol, sputum was obtained from 11 test subjects who were cystic fibrosis patients and not being treated with any medicament (designated below as CF group). Also, for testing with tyloxapol, sputum was obtained from 3 test subjects who were cystic fibrosis patients being treated with DNase (designated below as CF/with DNase group).

Additionally, for comparison testing with tyloxapol, sputum was obtained from 2 test subjects who were adult bronchiectases patients (designated below as AB group), and 3 test subjects who were healthy, normal, free of disease, persons (designated below as Control group). Moreover, as part of the comparison testing, sputum samples (CF, CF/with DNase, AB, and Control) were tested with saline.

Sputum samples were tested as follows. Sputum viscosity was studied using a Brookfield cone/plate viscometer (Brookfield Engineering Laboratories, Inc., Stoughton, Mass.). Sputum (750 microliters) was mixed 3:1 with 0.9% saline or with 0.125% tyloxapol in saline (250 microliters), vortexed 30 seconds, and then incubated 15 minutes at 37 degrees Centigrade. Because the initial viscosity of CF sputum of patients 1 and 9 was too high for measurement, their CF sputum was diluted 1:3 and 1:1, respectively, with saline or tyloxapol in saline.

The results clearly illustrated that for sputum from the CF group, tyloxapol had a dramatic effect in decreasing the viscosity as compared to simple dilution of sputum with saline, (i.e., sputum mean average viscosity went down 32.3 cp, that is from 44.7 cp for saline down to 12.4 cp for tyloxapol with saline for the CF group), but for sputum from the AB group, tyloxapol was largely ineffective in decreasing the viscosity as compared to simple dilution of sputum with saline, (i.e., sputum mean average viscosity went down only 2.7 cp, that is from 6.9 cp for saline down to 4.2 cp for tyloxapol with saline). The results are summarized in Table IV below.

TABLE IV

Effect of Tyloxapol on Viscosity of Sputum

| Test Subject | | Sputum Viscosity in Centipoise (mPa-s) at 0.3 RPM | |
|---|---|---|---|
| Group | No. | Saline | Tyloxapol in Saline |
| CF | | | |
| | 1 | 19.1 | 1.5 |
| | 2 | 49.0 | 6.1 |
| | 3 | 51.3 | 30.6 |
| | 4 | 88.7 | 31.4 |
| | 5 | 153.3 | 49.8 |
| | 6 | 35.2 | 1.5 |
| | 7 | 26.1 | 6.9 |
| | 8 | 10.8 | 2.3 |
| | 9 | 7.7 | 1.5 |
| | 10 | 15.4 | 3.1 |
| | 11 | 34.6 | 1.5 |
| Mean Average | | 44.7 ± 12.9 | 12.4 ± 5.1 |
| CF with DNase | | | |
| | 1 | 10.0 | 9.2 |
| | 2 | 6.9 | 4.6 |
| | 3 | 4.6 | 1.5 |
| Mean Average | | 7.2 ± 1.6 | 5.1 ± 2.2 |
| AB | | | |
| | 1 | 6.9 | 3.8 |
| | 2 | 6.9 | 4.6 |
| Mean Average | | 6.9 | 4.2 |
| Control | | | |
| | 1 | 3.1 | 1.5 |
| | 2 | 0 | 0 |
| | 3 | 8.4 | 0 |
| Mean Average | | 3.8 ± 2.5 | 0.5 ± 0.5 |

Thus, tyloxapol is a potent agent for decreasing viscosity of cystic fibrosis sputum, and should be useful in preventing injury of the airway in diseases such as cystic fibrosis. Administration of tyloxapol by tracheal installation to cystic fibrosis patients should work for mucociliary clearance of sputum produced in these patients and therefore protect them from injury. The result should be even better if some cetyl alcohol is admixed with the tyloxapol; preferably, the cetyl alcohol is added in 1 to 1.5 times the weight of the tyloxapol. Preparation of samples for administration to the patient should be the same as described above in the "DETAILED DESCRIPTION OF THE INVENTION" section herein, most preferably inhalation of 3 ml of a 0.125% solution of tyloxapol by jet aerosol every 4 to 6 hours.

EXAMPLE V

Suppression of Cytokine Production by Tyloxapol as Related to Cystic Fibrosis Patients Cachexia and/or anorexia prominent in patients with severe cystic fibrosis lung disease is caused by an increased rate of tumor necrosis factor (TNF) gene transcription and secretion by cystic fibrosis macrophages. (See, Pfeffer, Huecksteadt, and Hoidal, "Expression and Regulation of Tumor Necrosis Factor in Macrophages from Cystic Fibrosis Patients," *Am. J. Respir. Cell. Mol. Biol.* (1993) 9:511–519.) Tyloxapol should also ameliorate this aspect of adverse cystic fibrosis pathophysiology when administered to cystic fibrosis patients because, as shown below, it is a potent suppressant of TNF secretion by monocyte-macrophage cell lines.

Monocytes were prepared by mixing venous blood of healthy human volunteers with an equal volume of sterile isotonic saline/10 mM HEPES. The mixture was placed into 50 ml conical polyporpylene tubes in 30 ml aliquots. Each aliquot of diluted blood was underlayed with 20 to 25 ml of sterile Lymphocyte Separation Medium (LSM; Organon-Technika, Durham, N.C.).

The tubes were centrifuged at 400 g for 40 minutes at room temperature. The mononuclear cells at the interface were removed and washed twice in sterile isotonic saline/10 mM HEPES, followed by a wash in RPMI-1640. Purified monocytes were suspended at $2 \times 10^6$ cells/ml in RPMI supplemented with 100 U/ml penicillin, 100 ug/ml streptomycin, 2 mM L-glutamine, 1 mM pyruvate, 1% non-essential amino acids, 25 mM HEPES, and 5% heat-inactivated human serum.

To each well of a 48-well flat bottomed tissue culture plate was added 0.5 ml of cell suspension. Tyloxapol (diluted in complete medium at 4X the desired final concentration) was added in 250 ul volumes to each well. Control wells received 250 ul of complete medium.

Cell suspensions were incubated 16 hours at 37 degrees C. in humidified 5% carbon dioxide in the presence or absence of 100 ng/ml *Salmonella typhosa* lipopolysaccharide as a stimulant of cytokine production.

After incubation, supernatants were aspirated off, and the unattached cells and cell debris were removed by filtration. The release of cytokines was determined in the cell free supernatants using ELISA capture assays. The concentration of tyloxapol effective at inhibiting secretion of each tested cytokine by 50% ($EC_{50}$) is summarized in Table V below (interleukin is abbreviated as IL).

TABLE V

Tyloxapol Inhibition of Monocyte Cytokine Production

| Cytokine | $EC_{50}$ (mcg/ml) |
| --- | --- |
| TNF-alpha | 30 |
| IL1-beta | 60 |
| IL-6 | 30 |
| IL-8 | 70 |

Thus, tyloxapol, as a potent inhibitor of monocyte TNF secretion, should ameliorate the cachexia and/or anorexia suffered by patients with cystic fibrosis lung disease. Also, because interleukin-8 (IL-8) is an important chemotactic mediator perpetuating inflammation in the airway of cystic fibrosis patients (see, Nakamura, Yoshimura, McElvaney, and Crystal, "Neutrophil Elastase in Respiratory epithelial Lining Fluid of Individuals with Cystic Fibrosis Induces Interleukin-8 Gene Expression in a Human Bronchial Epithelial Cell Line," *J. Clin. Invest.* (1992) 89:1478–1484; and McElvaney, Nakamura, and Birrer, "Modulation of Airway Inflammation in Cystic Fibrosis. In Vivo Suppression of Surface by Aerosolization of Recombinant Secretory Leucoprotease Inhibitor," *J. Clin. Invest.* (1992) 90:1296–1301), tyloxapol should also reduce airway injury by inhibiting local production of the chemoattractant IL-8.

Hence, administration of tyloxapol by tracheal installation to cystic fibrosis patients should work as a potent inhibitor of monocyte TNF secretion, and should ameliorate the cachexia and/or anorexia suffered by patients with cystic fibrosis lung disease and should also reduce airway injury by inhibiting local production of the chemoattractant IL-8, and should therefore protect the cystic fibrosis patients from injury. The result should be even better if some cetyl alcohol is admixed with the tyloxapol; preferably, the cetyl alcohol is added in 1 to 1.5 times the weight of the tyloxapol. Preparation of samples for administration to the patient should be the same as described above in the "DETAILED DESCRIPTION OF THE INVENTION" section herein, most preferably inhalation of 3 ml of a 0.125% solution of tyloxapol by jet aerosol every 4 to 6 hours.

The appended claims set forth various novel and useful features of the invention.

What is claimed is:

1. A method for the treatment of cystic fibrosis disease resultant from overproduction of HOCl, said method comprising:

administering to a mammal having cystic fibrosis disease a compound selected from the following:

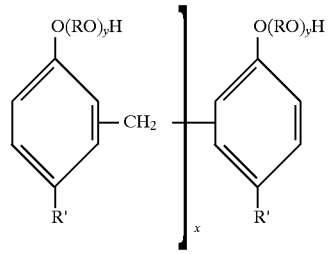

where, R is ethylene, R' is tertiary octyl, x is greater than 1, and y is 8 to 18, said compound being administered in an amount effective to inhibit oxidant chemical reactions caused by the HOCl in the mammal, said administering being done in a physiologically acceptable carrier, thereby treating the cystic fibrosis disease.

2. The method of claim 1, wherein said administering comprises administering said compound directly into the mammal's respiratory tract.

3. The method of claim 1, wherein said administering comprises administering said compound directly by aerosolization.

4. The method of claim 1, wherein said carrier is a physiologically buffered solution.

5. The method of claim 4, wherein said carrier is selected from the group consisting of isotonic saline, normal saline, and combinations thereof.

* * * * *

UNITED STATES PATENT AND TRADEMARK OFFICE
CERTIFICATE OF CORRECTION

PATENT NO. : 5,830,436
DATED     : November 3, 1998
INVENTOR(S) : Ghio et al.

It is certified that error appears in the above-identified patent and that said Letters Patent is hereby corrected as shown below:

On the title page,

In the Inventors' names, "Piantadcsi" should read --Piantadosi--.

Signed and Sealed this

Fourth Day of May, 1999

Attest:

Q. TODD DICKINSON

*Attesting Officer*   Acting Commissioner of Patents and Trademarks